US012758537B2

(12) United States Patent
Ivanov

(10) Patent No.: US 12,758,537 B2
(45) Date of Patent: Oct. 13, 2026

(54) INCREASED E-CADHERIN EXPRESSION FOR THE TREATMENT OF INFLAMMATORY DISEASES WITH INTESTINAL MUCOSAL INJURY

(71) Applicant: The Cleveland Clinic Foundation, Cleveland, OH (US)

(72) Inventor: Andrei Ivanov, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 291 days.

(21) Appl. No.: 17/370,165

(22) Filed: Jul. 8, 2021

(65) Prior Publication Data

US 2022/0008402 A1 Jan. 13, 2022

Related U.S. Application Data

(60) Provisional application No. 63/050,622, filed on Jul. 10, 2020.

(51) Int. Cl.

*A61K 9/00* (2006.01)
*A61K 9/28* (2006.01)
*A61K 31/4439* (2006.01)
*A61P 1/00* (2006.01)
*A61P 29/00* (2006.01)

(52) U.S. Cl.

CPC ........ *A61K 31/4439* (2013.01); *A61K 9/0053* (2013.01); *A61K 9/28* (2013.01); *A61P 1/00* (2018.01); *A61P 29/00* (2018.01)

(58) Field of Classification Search

None

See application file for complete search history.

(56) References Cited

U.S. PATENT DOCUMENTS

2005/0129676 A1 6/2005 Blaschuk et al.
2016/0052895 A1 2/2016 Lindsley et al.
2016/0052896 A1 2/2016 Lindsley et al.
2020/0246488 A1* 8/2020 Daly ........................ A61P 43/00

FOREIGN PATENT DOCUMENTS

WO WO 1994/011401 5/1994
WO WO2017160878 A1 9/2017
WO WO2020243616 A1 12/2020

OTHER PUBLICATIONS

Brogan et al.Optimization of a small molecule probe that restores e-cadherin expression. Bioorganic & Medicinal Chemistry Letters 25 (2015) 4260-4264 (Year: 2015).*

Karayiannakis et al. Expression of catenins and E-cadherin during epithelial restitution in inflammatory bowel disease J. Pathology, 184:413-418. Aug. 1998 (Year: 1998).*

Schnoor et al.E-cadherin Is Important for the Maintenance of Intestinal Epithelial Homeostasis Under Basal and Inflammatory Conditions. Dig. Dis Sci, 60:816-818, 2015 (Year: 2015).*

Li et al. E-cadherin plays an essential role in collective directional migration of large epithelial sheets. Cell. Mol. Life Sci, 2012,69:2779-2789 (Year: 2012).*

Bondow et al., E-cadherin is required for intestinal morphogenesis in the mouse. Dev Biol. Nov. 1, 2012;371(1):1-12.

Bron et al., Can probiotics modulate human disease by impacting intestinal barrier function? Br J Nutr. Jan. 2017;117(1):93-107.

Carvalho et al., Lack of microRNA-101 causes E-cadherin functional deregulation through EZH2 up-regulation in intestinal gastric cancer. J Pathol. Sep. 2012;228(1):31-44.

Chen et al., miR-200b inhibits TGF-β1-induced epithelial-mesenchymal transition and promotes growth of intestinal epithelial cells. Cell Death Dis. Mar. 14, 2013;4(3):e541. 8 pages.

Greenspon et al., Sphingosine-1-phosphate regulates the expression of adherens junction protein E-cadherin and enhances intestinal epithelial cell barrier function. Dig Dis Sci. May 2011;56(5):1342-53.

Gulei et al., The silent healer: miR-205-5p up-regulation inhibits epithelial to mesenchymal transition in colon cancer cells by indirectly up-regulating E-cadherin expression. Cell Death Dis. Jan. 19, 2018;9(2):66. 16 pages.

Hirano et al., Identification of novel small compounds that restore E-cadherin expression and inhibit tumor cell motility and invasiveness. Biochem Pharmacol. Nov. 15, 2013;86(10):1419-29.

Konermann et al., Genome-scale transcriptional activation by an engineered CRISPR-Cas9 complex. Nature. Jan. 29, 2015;517(7536):583-8.

Li et al., 5-Azacytidine suppresses EC9706 cell proliferation and metastasis by upregulating the expression of SOX17 and CDH1. Int J Mol Med. Oct. 2016;38(4):1047-54.

Li et al., Formononetin attenuated allergic diseases through inhibition of epithelial-derived cytokines by regulating E-cadherin. Clin Immunol. Oct. 2018;195:67-76.

Li et al., Upregulation of E-cadherin expression mediated by a novel dsRNA suppresses the growth and metastasis of bladder cancer cells by inhibiting β-catenin/TCF target genes. Int J Oncol. Jun. 2018;52(6):1815-1826.

Liu et al., Exosome-transmitted miR-128-3p increase chemosensitivity of oxaliplatin-resistant colorectal cancer. Mol Cancer. Mar. 19, 2019;18(1):43. pp. 1-17.

Menezes et al., The metastasis suppressor, NDRG1, attenuates oncogenic TGF-β and NF-κB signaling to enhance membrane E-cadherin expression in pancreatic cancer cells. Carcinogenesis, vol. 40, Issue 6, Jun. 2019, pp. 805-818.

(Continued)

*Primary Examiner* — Susan T Tran

(74) *Attorney, Agent, or Firm* — Jason R. Bond; Casimir Jones, S.C.

(57) ABSTRACT

Provided herein are methods and systems employing agents that up-regulate E-cadherin, or E-cadherin agonists, for the treatment of inflammatory diseases, such as inflammatory bowel diseases (e.g., Crohn's disease). In certain embodiments, the agent employed is ML327, E-cadherin Upregulator (ECU), or a compound of Formula I or II.

7 Claims, 9 Drawing Sheets

(56) References Cited

OTHER PUBLICATIONS

Petrova et al., Conformational epitopes at cadherin calcium-binding sites and p120-catenin phosphorylation regulate cell adhesion. Mol Biol Cell. Jun. 2012;23(11):2092-108.
Shashikanth et al., Allosteric Regulation of E-Cadherin Adhesion. J Biol Chem. Aug. 28, 2015;290(35):21749-61.
Wang et al., MicroRNA-122 triggers mesenchymal-epithelial transition and suppresses hepatocellular carcinoma cell motility and invasion by targeting RhoA. PLoS One. Jul. 3, 2014;9(7):e101330. 10 pages.
Wei et al., Up-regulation of microRNA-302a inhibited the proliferation and invasion of colorectal cancer cells by regulation of the MAPK and PI3K/Akt signaling pathways. Int J Clin Exp Pathol. May 1, 2015;8(5):4481-91.
Yang et al., miR-200b-containing microvesicles attenuate experimental colitis associated intestinal fibrosis by inhibiting epithelial-mesenchymal transition. J Gastroenterol Hepatol. Dec. 2017;32(12):1966-1974.
Alves et al., In a rat exclusion-colitis model, infliximab treatment increased colonic E-cadherin and claudin-3 levels in parallel with mucosal healing, Arq Bras Cir Dig. 34(4):e1639 (Jan. 31, 2022).
Bandyopadhyay et al., E-cadherin activating antibodies limit barrier dysfunction and inflammation in mouse inflammatory bowel disease. Tissue Barriers. 9(4):1940741 (Oct. 2, 2021).
Becker et al., Overexpression of CD97 in intestinal epithelial cells of transgenic mice attenuates colitis by strengthening adherens junctions. *PLoS One* 5:e8507 (2010).
Demetter et al., Focal up-regulation of E-cadherin-catenin complex in inflamed bowel mucosa but reduced expression in ulcer-associated cell lineage. Am J Clin Pathol. 114(3):364-70 (Sep. 2000).
Efstathiou et al., Intestinal trefoil factor controls the expression of the adenomatous polyposis coli-catenin and the E-cadherin-catenin complexes in human colon carcinoma cells. Proc Natl Acad Sci U S A. 95(6):3122-7 (Mar. 17, 1998).
Gassler et al., Inflammatory bowel disease is associated with changes of enterocytic junctions. Am J Physiol Gastrointest Liver Physiol. 281(1):G216-28 Jul. 2001).
Gordon et al., Proteolytic processing of the epithelial adherens junction molecule e-cadherin by neutrophil elastase generates short peptides with novel wound-healing bioactivity. Cell Mol Gastroenterol Hepatol. 7(2):483-486.e8 (2019).
Hanby et al., Downregulation of E-cadherin in the reparative epithelium of the human gastrointestinal tract. Am J Pathol. 148(3):723-9 (Mar. 1996).
Hermiston et al., Forced expression of E-cadherin in the mouse intestinal epithelium slows cell migration and provides evidence for nonautonomous regulation of cell fate in a self-renewing system. *Genes and Development*, 10(8), 985-996 (1996).
Hermiston et al., Dominant-negative cadherin in mouse intestine causes loss of E-cadherin, leading to chronic intestinal inflammation and neoplasia, *Science* 270:1203-1207 (1995).
Hunter et al., Polarized E-cadherin endocytosis directs actomyosin remodeling during embryonic wound repair. J Cell Biol. 210(5):801-16 (Aug. 31, 2015).
Jankowski et al., Alterations in classical cadherins associated with progression in ulcerative and Crohn's colitis. Lab Invest. 78(9):1155-67 (Sep. 1998) (Abstract Only).
Kucharzik et al., Neutrophil transmigration in inflammatory bowel disease is associated with differential expression of epithelial intercellular junction proteins. Am J Pathol. 159(6):2001-9 (Dec. 2001).
Mehta et al., Defects in the adherens junction complex (E-cadherin/β-catenin) in inflammatory bowel disease. Cell Tissue Res. 360(3):749-60 (Jun. 2015).

* cited by examiner

INCREASED E-CADHERIN EXPRESSION FOR THE TREATMENT OF INFLAMMATORY DISEASES WITH INTESTINAL MUCOSAL INJURY

The present application claims priority to U.S. Provisional application Ser. No. 63/050,622 filed Jul. 10, 2020, which is herein incorporated by reference in its entirety.

This invention was made with government support under DK108278 awarded by the National Institutes of Health. The government has certain rights in the invention.

FIELD

Provided herein are methods and systems employing agents that up-regulate E-cadherin, or E-cadherin agonists, for the treatment of inflammatory diseases, such as inflammatory bowel diseases (e.g., Crohn's disease and ulcerative colitis). In certain embodiments, the agent employed is ML327, E-cadherin Up-regulator (ECU), or a compound of Formula I or II.

BACKGROUND

Patients suffering from inflammatory bowel disease (IBD) experience varying degrees of abdominal pain, discomfort and recurring episodes of bloody diarrhea. This may be caused by pathogenic colonization, activation of the immune system, or genetic causes that result in varying medical conditions. IBD affects approximately 1.6 million patients in the United States of which 80,000 of those are children. This results in a staggering direct cost for patient related issues that ranges from $11-28 billion annually. However, a specific form of IBD, namely Crohn's Disease (CD), is more menacing and presents dire consequences even if timely medical intervention is initiated. CD affects a wide swath of ethnicities but is more common in Caucasian and African-American populations, less common in Latino and Asian populations, and people of Ashkenazi descent are at 4-5 higher risk than the general population.

CD typically affects the entire length and circumference of the small intestine and the upper large intestine. The disease manifests itself in the form of patchy lesions that are sporadically located along the intestines and penetrate the full thickness of the tissue itself. At the onset of the disease, the intestinal tissue progresses through several stages of inflammation which becomes increasingly worse over time. In normal situations, the body uses the inflammatory response to combat a variety of foreign insults as well as participate in body homeostasis at multiple levels. However, when the inflammatory response becomes unmanageable by the body, due to a number of factors, severe tissue damage and/or tissue death occurs. Manifestations of the disease include continual abdominal pain, bleeding and tissue rupturing, nutrient malabsorption, poor overall body growth and development, repeated surgical procedures, and the potential of intestinal cancer. Quality of life issues relating to CD range from depression, negative body image issues and social stigmas, and the negative impact on professional and family lifestyles. These attributes further contribute to the overall deterioration of this patient population.

Treatment options available to CD patients range from prescribed oral medications to biological reagents specifically designed to combat the hyperactive inflammatory response. However, a large percentage of the CD population that responds poorly to these treatment options, if at all. Further problems with current treatment options are that they are quite expensive, are inefficient, and have numerous side effects including the potential of inducing different types of cancer. CD patients experience recurrent flare-ups and typically require a highly invasive surgery to remove the dying or dead tissue. It is estimated that 70% of those with CD will require surgery over their lifetime and 30% and 60% of those will require additional surgery at 3 and 10 years post-initial surgery, respectively. There still exists an unmet clinical need to address the issues surrounding the highly pro-inflammatory local environment in CD patients.

SUMMARY

Provided herein are methods and systems employing agents that up-regulate E-cadherin, or E-cadherin agonists, for the treatment of inflammatory diseases, such as inflammatory bowel diseases (e.g., Crohn's disease). In certain embodiments, the agent employed is ML327, E-cadherin Up-regulator (ECU), or a compound of Formula I or II.

In some embodiments, provided herein are methods of treating an inflammatory condition comprising: administering to a subject (e.g., human subject) a composition comprising: i) an agent that up-regulates the expression of E-cadherin, and/or ii) an E-cadherin agonist, wherein the subject has an inflammatory condition.

In certain embodiments, provided herein are compositions or articles of manufacture comprising: a) a composition comprising a pharmaceutically acceptable carrier and i) an agent that up-regulates the expression of E-cadherin, and/or ii) an E-cadherin agonist; wherein the composition is in the form of a pill for oral ingestion by a human subject, and b) a delayed release coating covering the pill form such that all or most of the agent or agonist is released in the bowels of the subject upon oral ingestion.

In particular embodiment, provided herein are compositions shaped for use as a suppository in a human, wherein the composition comprises a pharmaceutically acceptable carrier and i) an agent that up-regulates the expression of E-cadherin, and/or ii) an E-cadherin agonist. In some embodiments, the pharmaceutically acceptable carrier is formulated for release of the agent and/or the agonist in the bowel of the human.

In certain embodiments, provided herein are compositions shaped for oral ingestion in a human, wherein said composition comprises a pharmaceutically acceptable carrier and i) an agent that up-regulates the expression of E-cadherin, and/or ii) an E-cadherin agonist. In particular embodiments, the pharmaceutically acceptable carrier is formulated for delayed release of the agent and/or agonist in the bowel of said human after oral administration.

In other embodiments, provided herein are systems comprising: a) a composition described herein, and b) a medical device for administering the composition to a site of inflammation within the bowels of a subject. In certain embodiments, the medical device comprises a syringe, catheter, or endoscope.

In some embodiments, the inflammatory condition is a gut inflammatory condition. In other embodiments, the inflammatory condition is inflammatory bowel disease (e.g., Crohn's disease and ulcerative colitis). In certain embodiments, an agonist (e.g., E-cadherin activating antibodies or biologically active fragments thereof) are administered to the patient intravenously.

In particular embodiments, the agent is small molecule ML327 (N-(3-(2-hydroxynicotinamido) propyl)-5-phenylisoxazole-3-carboxamide), which has the following structure:

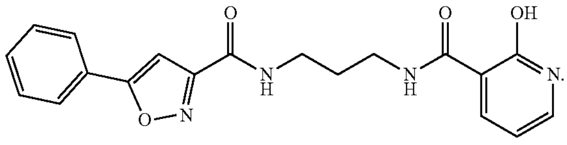

ML327

In other embodiments, the agent is small molecule E-cadherin Up-Regulator (ECU; 5-(Furan-2-yl)-N-(pyridine-4-yl) butyl)isoxazole-3-carboxamide), which has the following structure:

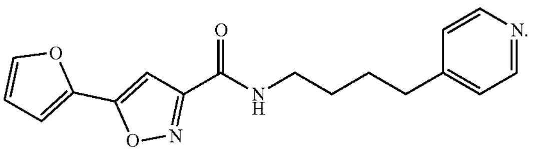 [SMILES: O=C(NCCCCc1ccncc1)c1cc(-c2ccco2)on1]

In particular embodiments, the agent is any of the compounds described in US Pat. Pub. 20160052895 (herein incorporated by reference in its entirety), including as shown in Formula I below:

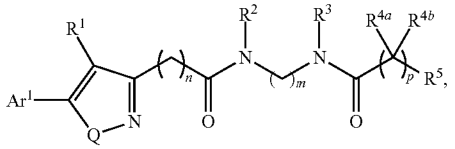

wherein m is an integer selected from 2, 3, and 4; wherein n is an integer selected from 0 and 1; wherein p is an integer selected 0, 1, and 2; wherein Q is selected from $NR^6$, O, and S; wherein $R^6$ is selected from hydrogen and C1-4 alkyl; wherein $R^1$ is selected from hydrogen and C1-C4 alkyl; wherein each of $R^2$ and $R^3$ is independently selected from hydrogen and C1-C4 alkyl; wherein each occurrence of $R^{4a}$ and $R^{4b}$ is independently selected from hydrogen, halogen, —OH, —CN, —$N_3$, —$NH_2$, and C1-C4 alkyl, or wherein each of $R^{4a}$ and $R^{4b}$ are optionally covalently bonded and, together with the intermediate atoms, comprise a 3- to 5-membered cycle; wherein $R^5$ is selected from $Cy^2$ and $Ar^2$; wherein $Cy^2$, when present, is selected from cycloalkyl and heterocycloalkyl, and $Cy^2$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino, provided that when m is 2 then $Cy^2$ is not cycloalkyl; wherein $Ar^2$, when present, is selected from aryl and heteroaryl, and $Ar^2$ is substituted with 0, 1, 2, or 3 substituents independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, C1-C4 dialkylamino, $Cy^3$, $Ar^3$, and —NH(C═O)(C1-C4 alkyl)$Cy^3$, provided that when m is 2 then $Ar^2$ is not substituted or unsubstituted phenyl, substituted or unsubstituted furanyl, or substituted or unsubstituted pyridinyl; wherein $Cy^3$, when present, is selected from cycloalkyl and heterocycloalkyl, and $Cy^3$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; wherein $Ar^3$, when present, is selected from aryl and heteroaryl, and $Ar^3$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; provided that when m is 3, n is 0, and p is 0, that $Ar^2$, when present, is not a structure represented by a formula:

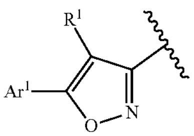

;

and wherein $Ar^1$, is selected from aryl and heteroaryl, and $Ar^1$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof.

In some embodiments, the agent is any of the compounds described in US Pat. Pub. 20160052896 (herein incorporated by reference in its entirety), including as shown in Formula II below:

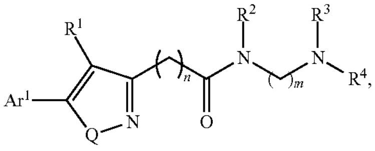

wherein m is an integer selected from 3 and 4; wherein n is an integer selected from 0 and 1; wherein Q is selected from $NR^5$, O, and S; wherein $R^5$, when present, is selected from hydrogen and C1-C4 alkyl; wherein each of $R^1$ and $R^2$ is independently selected from hydrogen and C1-C4 alkyl; wherein $R^3$ is selected from hydrogen and $(CHR^6)_pAr^2$; wherein p, when present, is an integer selected from 0 and 1; wherein $R^6$, when present, is selected from hydrogen and C1-C4 alkyl; wherein $Ar^2$; when present, is selected from aryl and heteroaryl, and $Ar^2$ is substituted with 0, 1, 2, or 3 groups independently selected from halogen, —OH, —CN, —$N_3$, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino; wherein $R^4$ is selected from $CH_2Ar^3$ and $Ar^4$; wherein $Ar^3$, when present, is selected from aryl and heteroaryl, and $Ar^3$ is substituted with 0, 1, 2, or 3 groups independently selected from halogen, —OH, —CN, —$N_3$, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino, provided that when $R^2$ is hydrogen then $Ar^3$, when present, cannot be a structure selected from:

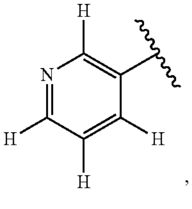

,

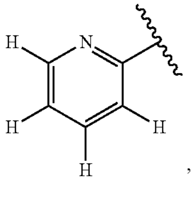

, and

-continued

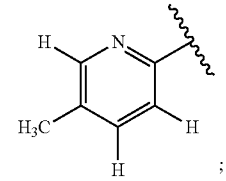

;

wherein $Ar^4$, when present, is selected from aryl and heteroaryl, and $Ar^4$ is substituted with 0, 1, 2, or 3 groups independently selected from halogen, —OH, —CN, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino, provided that when $R^2$ is hydrogen then $Ar^3$, when present, cannot be a structure selected from:

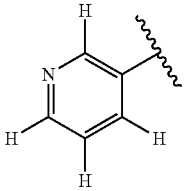

,

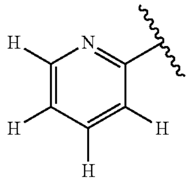

,

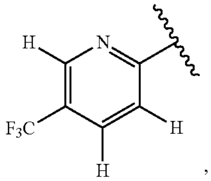

,

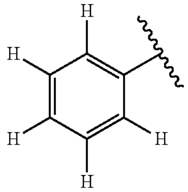

, and

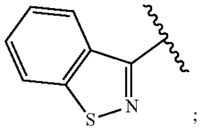

;

and wherein $Ar^1$, when present, is selected from aryl and heteroaryl, and wherein $Ar^1$, when present, is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof.

In certain embodiments, the subject is a human. In other embodiments, the composition is administered to the bowel of the subject. In further embodiments, the composition is administered systemically to the subject. In additional embodiments, the composition is administered locally to a site of inflammation in the subject. In other embodiments, the composition is formulated as a suppository and is administered rectally or a formulated as a delayed release pill for oral administration.

In particular embodiments, the composition comprises the agent. In other embodiments, the composition comprises the E-cadherin agonist. In other embodiments, the composition further comprises a pharmaceutically acceptable carrier.

DEFINITIONS

Figure 1:
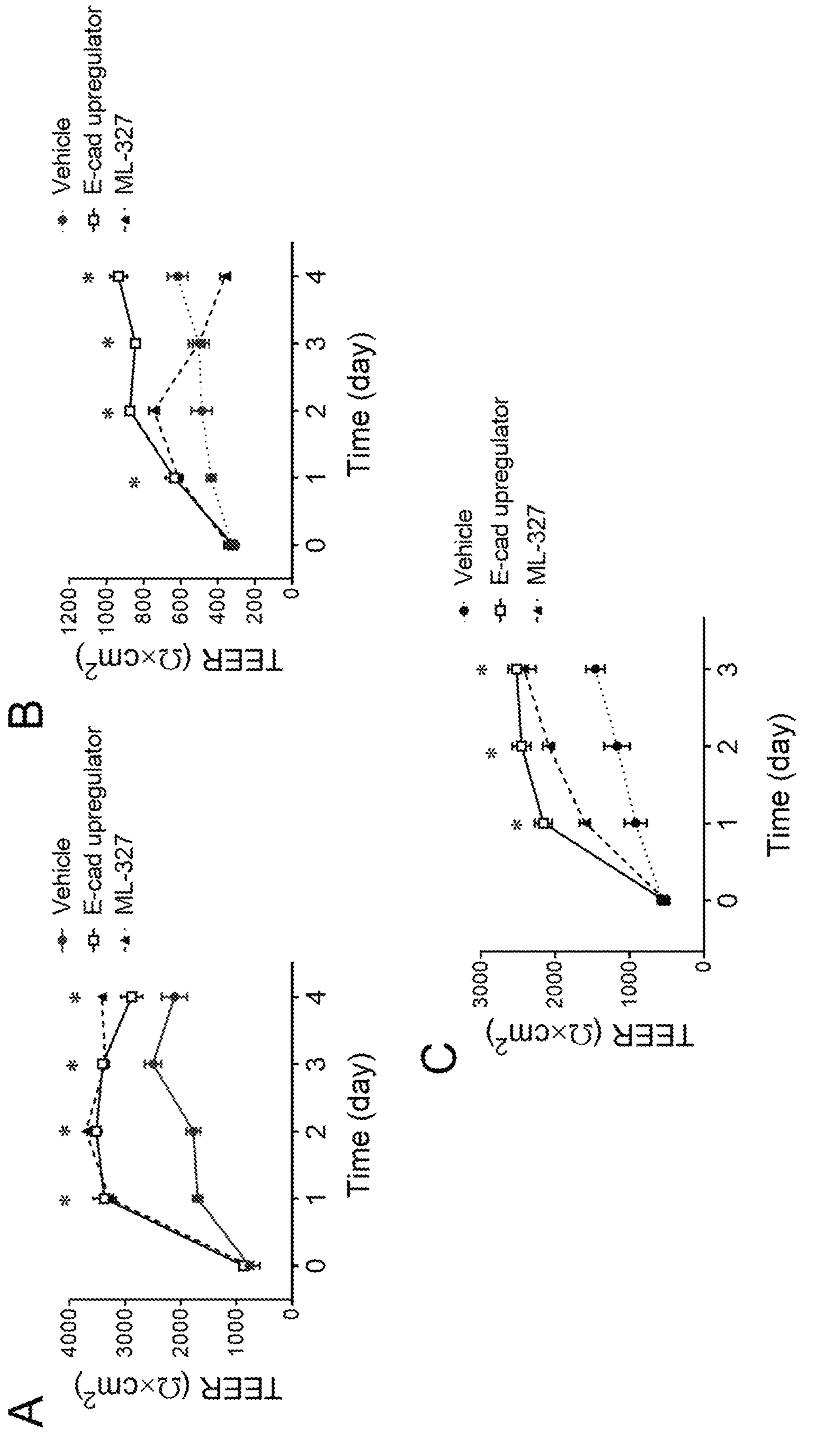
FIG. 1: E-cadherin-enhancing drugs decrease ionic permeability of model colonic epithelial cell monolayers. Confluent T84 (A), HT-29cF8 (B) and SK-0015 (C) cell monolayers were treated for indicated times with either vehicle, E-cadherin upregulator (ECU, 10 μM), or ML327 (10 μM). Transepithelial electrical resistance (TEER) of the cell monolayers was measured before and during the drug treatment. Data is presented as mean±SE (n=3); *P<0.05.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise.

As used herein, the term "pharmaceutically acceptable carrier" refers to non-toxic solid, semisolid, or liquid filler, diluent, encapsulating material, formulation auxiliary, or carrier conventional in the art for use with a therapeutic agent for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. A "pharmaceutical composition" typically comprises at least one active agent (e.g., ML327, E-cadherin Up-regulator (ECU), or a compound of Formula I or II) and a pharmaceutically acceptable carrier.

As used herein, the term "effective amount" refers to the amount of a composition (e.g., ML327, E-cadherin Up-regulator (ECU), or a compound of Formula I or II) sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., pharmaceutical compositions herein) to a subject or in vivo, in vitro, or ex vivo cells, tissues, and organs. Exemplary routes of administration to the human body can be through the eyes (e.g., intraocularly, intravitrealy, periocularly, ophthalmic, etc.), mouth (oral), skin (transdermal), nose (nasal), lungs (inhalant), oral mucosa (buccal), ear, rectal, by injection (e.g., intravenously, subcutaneously, intratumorally, intraperitoneally, etc.) and the like.

As used herein, the terms "co-administration" and "co-administer" refer to the administration of at least two agent(s) or therapies to a subject. In some embodiments, the co-administration of two or more agents or therapies is concurrent (e.g., in the same or separate formulations). In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s). An exemplary co-administration is a first agent selected from ML327, E-cadherin Up-regulator (ECU), or a compound of Formula I or II, and a second agent that is an agent used to treat IBD (e.g., an anti-inflammatory, such as a corticosteroids or aminosalicylate, such as mesalamine (Asacol HD, Delzicol, others), balsalazide (Colazal) and olsalazine (Dipentum)).

As used herein, the term "bowels" refers to the portions of the alimentary canal below the stomach, including the small intestine (e.g., jejunum, duodenum, ileum) and large intestine (e.g., cecum, ascending colon, transverse colon, descending colon, sigmoid colon).

The term bowel diseases includes, for example, irritable bowel syndrome (IBS), uncontrolled diarrhea-associated Irritable Bowel Syndrome (BIBS), Crohn's disease, traveler's diarrhea, ulcerative colitis, infectious enteritis, small intestinal bacterial overgrowth, celiac diseases, necrotizing enterocolitis, chronic and acute pancreatitis, sepsis, liver cirrhosis or other forms of hepatitis.

DETAILED DESCRIPTION

Provided herein are methods and systems employing agents that up-regulate E-cadherin, or E-cadherin agonists, for the treatment of inflammatory diseases, such as inflammatory bowel diseases (e.g., Crohn's disease). In certain embodiments, the agent employed is ML327, E-cadherin Up-regulator (ECU), or a compound of Formula I or II.

In certain embodiments, provided herein are agents for upregulation of a major epithelial junction protein, E-cadherin, or E-cadherin agonists, in order to stabilize the epithelial barrier (e.g., in a human subject), prevent inflammation-induced epithelial cell death and to promote mucosal restitution (e.g., wound healing) in inflamed gut, thus providing therapy for patients with various intestinal and systemic inflammatory disorders. Integrity and selective permeability of the intestinal epithelial barrier is essential for human health, since this barrier separates microbes in the gut lumen from the body immune system. Disruption of the gut barrier results in penetration of bacteria and/or their product into intestinal tissue and other internal organs that leads to immune cell activation, thereby triggering or exaggerating inflammatory responses. Disruption of the intestinal epithelial barrier is a common manifestation of different gastrointestinal diseases including inflammatory bowel disease (e.g., IBD, encompassing Crohn's disease and ulcerative colitis), celiac disease, irritable bowel syndrome and enteric infections. Furthermore, a number of recent studies suggests a broader role of the leaky intestinal epithelial barrier in the development of non-gastrointestinal immune or inflammatory disorders, such as type II diabetes, chronic liver failure, sepsis and trauma, asthma, etc. Therefore, provided herein are administered agent (e.g., small molecules, microRNA, etc.) approaches to enhance the barrier function of the intestinal epithelium and attenuate disruption of the gut barrier during inflammation.

Permeability of the intestinal epithelial barrier is determined by specialized cellular structures called junctions. Among several epithelial junctional complexes, adherens junctions appear to be the most important, since they initiate intercellular contacts and control the assembly of other junctions. E-cadherin is the major component of adherens junction and it is indispensable for the formation and maintenance of the intestinal epithelial barrier.

Work conducted during development of embodiments herein demonstrated unexpected activities of the E-cadherin up-regulator and ML327 that include: (i) decreased permeability of normal intestinal epithelial cell monolayers to small ions and large molecules; (ii) attenuation of the intestinal epithelial barrier disruption caused by classical proinflammatory cytokines, tumor necrosis factor-alpha (TNFa) and interferon-gamma (IFNy); inhibition of TNFa/IFNy-induced disassembly of epithelial tight junctions and adherens junctions; (iii) inhibition of TNFa/IFNy-induced apoptosis; (iv) stimulation of wound healing in intestinal epithelial cell monolayers.

In certain embodiments, any agent or compound that can upregulate the expression of E-cadherin can be tested to determine its ability to treat an inflammatory condition. In certain embodiments, isoxazole-based compounds are employed. In some embodiments, E-cadherin up-regulator (ECU), ML327, or a compound of Formula I or II are employed as epithelial barrier-protective and pro-restitutive therapeutic approach during intestinal inflammation and other diseases that are characterized by the disruption of the gut barrier. In certain embodiments, dsRNA is used to up-regulate E-cadherin, such as in dsRNA Li et al., 2018, International Journal of Oncology, 52, 1815-1826, herein incorporated by reference in its entirety. In certain embodiments, the agent used to up regulate E-cadherin is found in Hirano et al., Biochem Pharmacol 2013, 86: 1419-1429, which is herein incorporated by reference. Hirano et al. demonstrates stimulated E-cadherin expression with methotrexate and the following compounds:

284

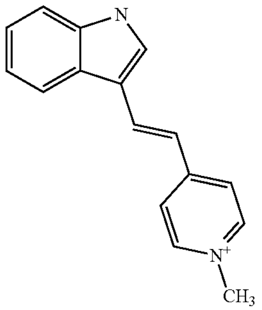

-continued

1427

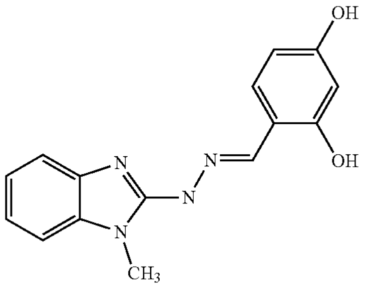

633

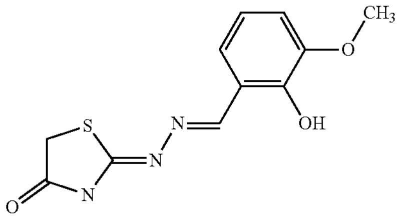

1883

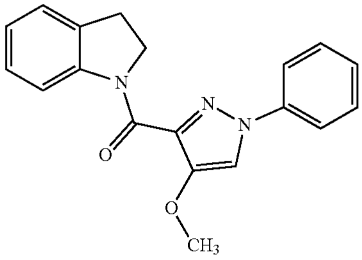

2870

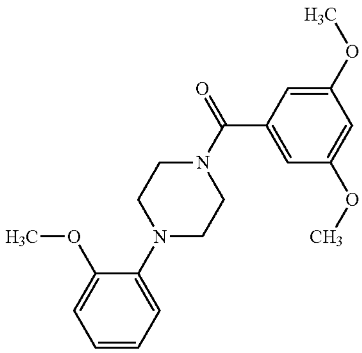

5709

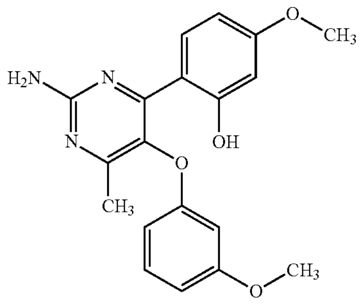

-continued

3693

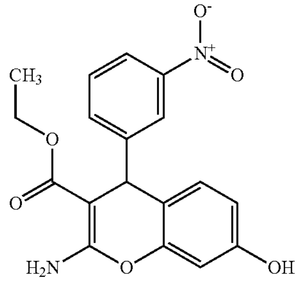

3445

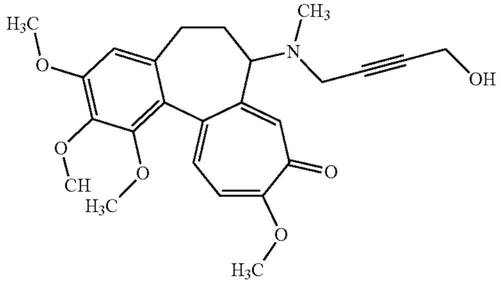

9301

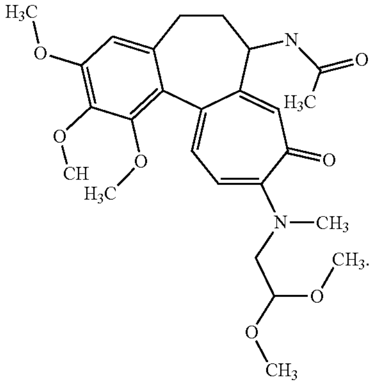

Other known compounds that stimulate E-cadherin expression include the following: i) 5-Axacytidine from Li et al. Int. J. Mol. Med. 2016, 38: 1047-54; ii) Sphingosine-1-Phosphate from Greenspon et al. Dig. Dis. Sci. 2011, 56: 1342-1353; iii) Formononetin, Li et al. Clinical Immunology 2018, 195: 67-76; and iv) Di(2-pyridyl)ketone 4,4-dimethyl-3-thiosemicarbazone (Dp44mT) and di(2-pyridyl) ketone 4-cyclohexyl-4-methyl-3-thiosemicarbazone (DpC) from Menezes et al., Carcinogenesis 2018, Dec. 18 (Epub ahead of print); all of these references are herein incorporated by reference in their entireties.

MicroRNAs that upregulate E-cadherin can also be used herein. Such microRNAs can, for example, be delivered into colonic epithelial cells in order to elevate E-cadherin expression in inflamed and injured intestinal mucosa. Examples of microRNAs (miR) that stimulate E-cadherin expression are: miR-200b (Yang et al. J. Gastroenterol. Hepatol. 2017, 12: 1966-1974; Chen, et al. Cell Death Dis. 2013, 4: e541), miR-205 (Gulei et al. Cell Death Dis. 2018, 9:66), miR-302a (Wei et al. Int J Clin Exp Pathol 2015, 8: 4481-4491), miR-122 (Wang et al. PLoS One, 2014, 9:e101330), miR-101 (Carvalho et al. J Pathol. 2012, 228: 31-44) and miR-128 (Liu et al. Mol Cancer 2019, 18:43). All of these references are herein incorporated by reference in their entireties. In other embodiments, CRISPR/Cas9 is employed to upregulate E-cadherin expression in a subject. For example, one implementation of this that could be used is called Synergistic Activation Mediator (SAM) technique and it uses a combination of Cas9, two transactivator proteins and sgRNA to provide robust and specific increase in transcription of endogenous genes of interest (Konermann et al. Genome-scale transcriptional activation by an engineered CRISPR-Cas9 complex. Nature 2015; 517(7536): 583-588).

In certain embodiments, the subject herein (e.g., with a gut disease) are administered an E-cadherin agonist. In certain embodiments, such agonist is a monoclonal E-cadherin-activating antibody or biologically active fragment thereof. Such activating antibodies interact with extracellular domains of E-cadherin, alter protein conformation and promote E-cadherin-based cell-cell adhesions (see, e.g., Petrova et al., Mol Cell Biol 2012, 11: 2092-2108; and Shashikanth et al. J Biol Chem 2015, 290: 21749-21761; both of which are herein incorporated by reference).

While the present invention is not limited to any particular mechanism, and an understanding of the mechanism is not necessary to practice the invention, the following is believed. Agent stimulation of E-cadherin expression, and agonist stimulation of E-cadherin activity, enhances barrier properties of normal intestinal epithelium and attenuates barrier disruption and epithelial junction disassembly caused by gut inflammation. Stimulation of E-cadherin expression or activity protects from epithelial cell death induced by inflammation, immune response and other injuries. Agent upregulation of E-cadherin stimulates wound healing in the intestinal epithelium thereby promoting restitution of the inflamed mucosa. Small molecules enhancing E-cadherin functions may have unique triple-beneficial (barrier-protective, pro-survival and pro-restitutive) effect during intestinal and other types of tissue inflammation, which make this a superior strategy comparing to the existing barrier-protecting approaches.

In certain embodiments, a subject is treated with an agent that upregulates E-cadherin (i.e., increase the expression in part of or all of the subject), or an agent that is an E-cadherin agonist, where the patient has a disorder selected from the group consisting of: inflammatory bowel disease, celiac disease, irritable bowel symptoms, sepsis and septic shock, burn injury and radiation-induced injury. In other embodiments, the subject has a non-intestinal inflammatory diseases, such as diabetes, liver failure, or asthma. In some embodiments, the subject has a gastrointestinal injury caused by different medications and or by chemotherapeutic agents or radiation treatment.

While the present invention is not limited to any particular mechanism and an understanding of the mechanism, it is believed at least some of the following benefits and advantages apply. First, upregulation of E-cadherin expression or activity will have multiple beneficial effects by stabilizing epithelial adherens and tight junctions, inhibiting epithelial cell death and stimulating wound healing. This combination of beneficial effects is especially important under conditions of chromic intestinal inflammation accompanied not only be increased intestinal permeability, but also significant epithelial cell death and ulcer formation. Second, the majority of existing barrier-protective strategies that include use of probiotic microorganisms and their metabolites, target tight junctions in the intestinal epithelium (Bron P A et al Brit J Nutrition 2017, 117 93-1 07). However, stabilization of tight junctions is insufficient to protect/restore epithelial barrier integrity in inflamed/injured gut where E-cadherin-based adherens junctions will remain disrupted. This may explain negative results of several clinical trials that used probiotic therapy in IBD patients. Oppositely, since E-cadherin-based adherens junctions have a commanding role in epithelial cell adhesion and regulate assembly of other junctional complexes, enhancing E-cadherin expression will accelerate formation and functions of all other junctions. Furthermore, tight junctions do not have such prominent anti-apoptotic and wound healing-promoting activity as compared to adherens junctions.

In particular embodiments, the compositions and methods herein find use in preventing or reducing inflammation and/or treating inflammatory bowel diseases (e.g., Crohn's disease and ulcerative colitis); however, applications are not so limited. Compositions and methods herein may find use more broadly in tissue regeneration applications (e.g., bowel tissue regeneration), other medical applications, or other non-medical materials applications.

Compositions and methods herein find use in a variety of applications. In particular, the E-cadherin expression enhancing agents herein (e.g., ECU, ML327, and compounds of Formula I or II) are administered (e.g., systemically or locally) for the treatment of inflammation-related conditions/diseases/disorders. In some embodiments, the small molecules herein are administered (e.g., systemically or locally) for the treatment of inflammation-related conditions/diseases/disorders in the bowel of a subject. In some embodiments, pharmaceutical compositions comprising the agents herein are administered topically or by injection to the site of treatment (e.g., site of inflammation (e.g., lesions)) in the bowels. In some embodiments, an endoscope (e.g., inserted through the rectum) is used to administer the agents herein to treatment sites within the bowels. In some embodiments, agents herein are formulated for rectal administration (e.g., as a suppository). In some embodiments, pharmaceutical compositions comprising the agents herein are administered rectally (e.g., as a suppository). In other embodiments, agents herein are administered systemically (e.g., orally, intravenously, etc.). In some embodiments, methods are provided herein for the treatment of one or more of irritable bowel syndrome (IBS), uncontrolled diarrhea-associated Irritable Bowel Syndrome (dIBS), Crohn's disease, traveler's diarrhea, ulcerative colitis, infectious enteritis, small intestinal bacterial overgrowth, celiac disease, necrotizing enterocolitis, chronic and acute pancreatitis, sepsis, hepatitis and liver cirrhosis, and/or symptoms (e.g., inflammation, lesions, etc.) related thereto. In some embodiments, the agents described herein are administered to a subject suffering from one of the aforementioned conditions. In some embodiments, the agents described herein are co-administered and/or co-formulated with other agents for the treatment of bowel diseases.

EXPERIMENTAL

Example 1

Small Molecule Up-Regulation of E-cadherin in Intestinal Epithelial Barrier Mode This example describes testing the activity of E-cadherin up-regulator (ECU) and ML327 in preclinical models of intestinal epithelial barrier disruption and restitution. The results demonstrated that these compounds enhance steady state barrier function in different human intestinal epithelial cell lines, attenuate cytokine-induced disruption of model epithelial barriers, inhibit cytokine-induced apoptosis and stimulate wound healing in human intestinal epithelial cell monolayers.

Measurement of Epithelial Barrier Permeability In Vitro

Transepithelial electrical resistance (TEER) of cultured T84, HT-29 and SK-C015 intestinal epithelial cell monolayers was measured using an EVOMX voltohmmeter (World Precision Instruments, Sarasota, FL). Cells were plated on collagen-coated transwell filters (pore size 3 μm, Thermo-Fisher). The resistance of cell-free collagen-coated filters was subtracted from each experimental point. An in vitro dextran flux assay was performed by a following commonly-used protocol. Intestinal epithelial cell monolayers growing on transwell filters were apically exposed to 1 mg/ml of FITC-labeled dextran (4,000 Da) in HEPES-buffered Hanks balanced salt solution (HBSS). After 120 min of incubation, HBSS samples were collected from the lower chamber, and FITC fluorescence intensity was measured using a Victor$^3$ V plate reader (Perkin Elmer, Waltham, MA) with excitation and emission wavelengths 485 and 544 nm, respectively. After subtracting the fluorescence of dextran-free HBSS the amount of FITC dextran translocated across the epithelial cell monolayer was calculated based on a calibration curve using Prism 5 software (GraphPad, La Jolla, CA).

Immunofluorescence Labeling, and Confocal Microscopy

In order to visualize structure of epithelial junctions, cultured colonic epithelial cell monolayers were fixed and permeabilized with 100% methanol at −20° C. Fixed samples were blocked for 60 min in HBSS containing 1% bovine serum albumin, followed by a 60-min incubation with primary antibodies against E-cadherin (BD Bioscience) and ZO-1 (Thermo-Fisher). Samples were then washed and incubated with Alexa-Fluor-488-conjugated donkey anti-rabbit and Alexa-Fluor-555—conjugated donkey anti-mouse secondary antibodies for 60 min, rinsed with blocking buffer, and mounted on slides with ProLong Antifade mounting reagent (Thermo-Fisher). Immunolabeled cell monolayers were imaged using a Leica SP8 confocal microscope (Wentzler, Germany). The Alexa Fluor 488 and 555 signals were acquired sequentially in frame-interlace mode to eliminate cross talk between channels. Images were processed using Adobe Photoshop. The images shown are representative of at least three experiments, with multiple images taken per slide.

Immunoblotting Analysis

To prepare total cell lysates, epithelial cell monolayers were scraped and homogenized using a Dounce homogenizer in RIPA buffer (20 mM Tris, 50 mM NaCl, 2 mM EDTA, 2 mM EGTA, 1% sodium deoxycholate, 1% Triton X-100 (TX-100), and 0.1% SDS, pH 7.4) containing protease inhibitor cocktail and phosphatase inhibitor cocktails 2 and 3 (Sigma-Aldrich). The obtained total cell lysates were cleared by centrifugation (20 min at 14,000×g), diluted with 2×SDS sample loading buffer and boiled. SDS-polyacrylamide gel electrophoresis was conducted using a standard protocol with equal amounts of total protein (10 or 20 μg) loaded per each lane. The separated proteins were transferred to nitrocellulose membranes and the membranes were blocked with 5% non-fat milk. The blocked membranes were incubated overnight with primary antibodies against total PARP, cleaved PARP and cleaved (active) caspase-3 (all from Cell Signaling), exposed to HRP-conjugated secondary antibodies for 1 hour, and the labeled proteins were visualized using a standard enhanced chemoluminescence solution and X-ray films.

Wound Healing Assay

Confluent epithelial cell monolayers were mechanically wounded by making a thin scratch wound with a 200 μl pipette tip. The bottom of the well was marked to define the position of the wound and the monolayers were supplied with fresh cell culture medium. The images of a cell-free area at the marked region were acquired at the indicated times after wounding using an inverted bright field microscope equipped with a camera. The percentage of wound closure was calculated using an Image J software (NIH, Bethesda, MD).

Description of the Results

Figure 2:
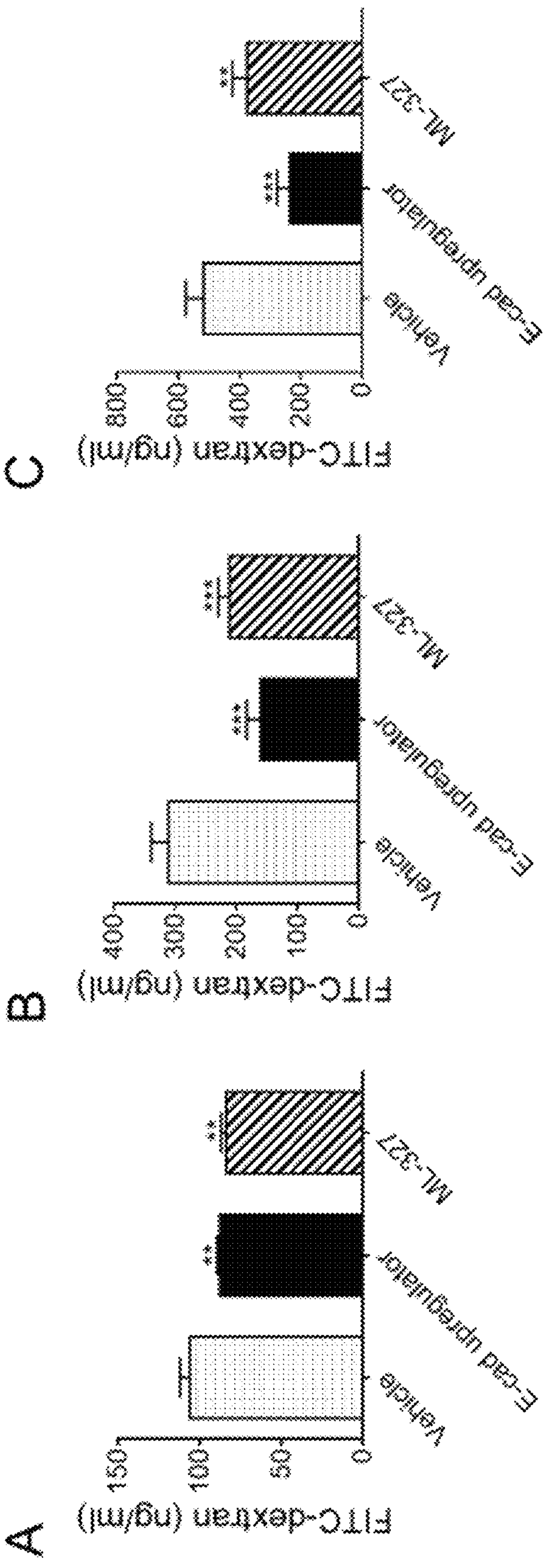
FIG. 2: E-cadherin-enhancing drugs decrease colonic epithelial permeability to large molecules. Confluent T84 (A), HT-29cF8 (B) and SK-C015 (C) cell monolayers were treated with either vehicle, ECU, or ML327, as described in the FIG. 1 legend. Trans-monolayer flux of FITC-dextran was determined at the end of the drug treatment. Data is presented as mean±SE (n=3); P<0.05 *P<0.01.

One set of experiments examined the effects of E-cadherin upregulator (ECU) and ML327 on the barrier properties of normal model intestinal epithelial cell monolayers. Three different human colonic epithelial cell lines, namely, T84, SK-0015 and HT-29 cF8 cells, were used. Cells were plated on collagen-coated transwell filters and allowed to reach confluency and differentiate for 5-7 days after plating. Thereafter, cell monolayers were exposed to either ECU (10 μM), ML327 (10 μM) or vehicle (DMSO). Transepithelial electrical resistance (TEER) was measured before and at different times after addition of E-cadherin-enhancing drugs. A transepithelial flux of FITC-dextran was examined at the end of the drug exposure to evaluate epithelial permeability to large uncharged molecules. Both ECU and ML327 caused a rapid (within 24 h) and sustained (up to 96 h) increase in TEER of all tested epithelial cell monolayers, which reflects decreases epithelial permeability to small ions (FIG. 1). One exception was the effect of ML327 on HT29 cell monolayers, where the drug transiently increased TEER for the first 48 hours with its subsequent decrease at later times (FIG. 1B). Furthermore, ECU and ML327 exposure significantly inhibited FITC-dextran flux in all three colonic epithelial cell lines, thereby indicating attenuated epithelial permeability to large molecules (FIG. 2). Together, these results demonstrate that E-cadherin-enhancing drugs promote barrier functions in well-differentiated human intestinal epithelial cell monolayers.

Figure 3:
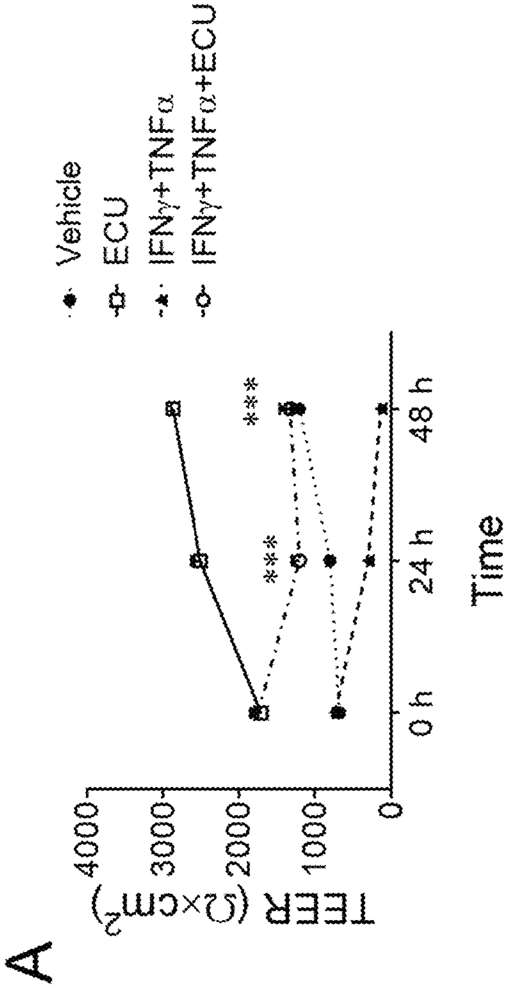
FIG. 3: E-cadherin upregulator (ECU) prevents cytokine-induced disruption of the model intestinal epithelial barrier. Confluent T84 cell monolayers were pretreated with either vehicle, or ECU (10 μM) for 24 h. Afterwards, cells were exposed to a combination of TNFα (10 ng/ml) and IFNγ (50 ng/ml) with and without ECU. (A) TEER was measured at the indicated times. (B) FITC-dextran flux was examined after 48 h incubation with cytokines. Data is presented as mean±SE (n=3); ***P<0.001.
Figure 3:
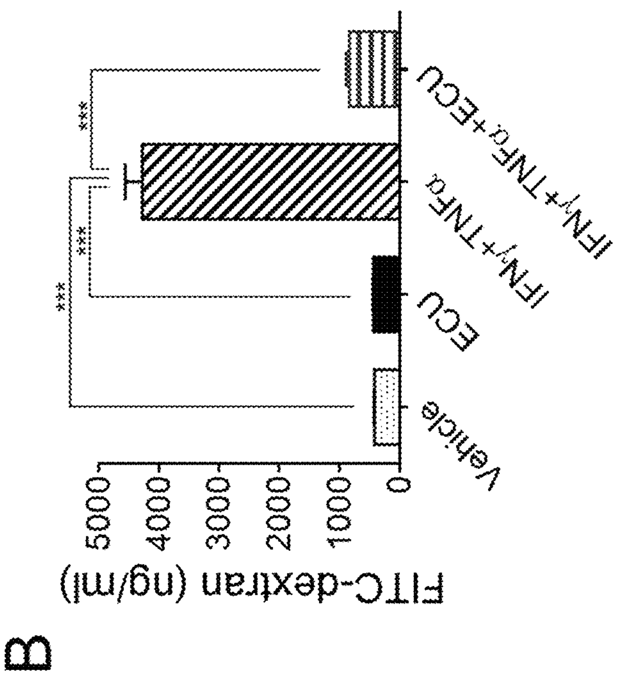
Figure 4:
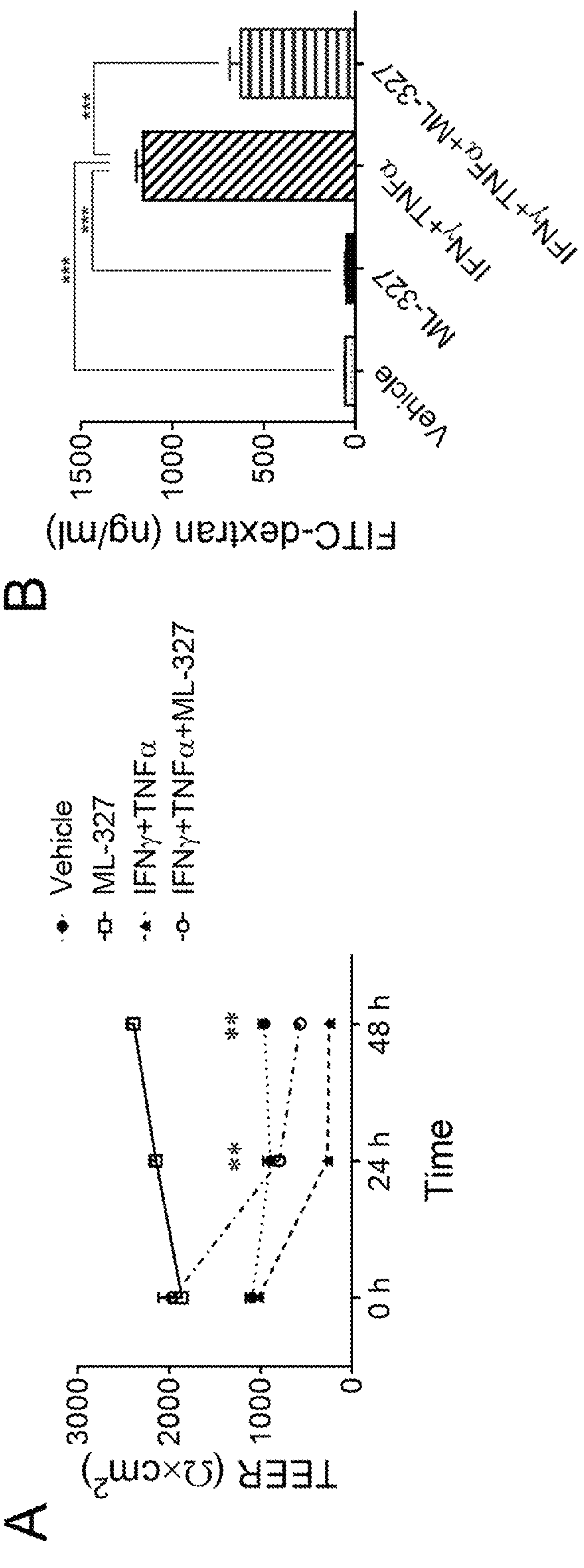
FIG. 4: ML327 prevents cytokine-induced disruption of the model intestinal epithelial barrier. Confluent T84 cell monolayers were pretreated with either vehicle, or ML327 (10 μM) for 24 hours. Afterwards, cells were exposed to a combination of TNFα (10 ng/ml) and IFNγ (50 ng/ml) with and without ML327. (A) TEER was measured at the indicated times. (B) FITC-dextran flux was examined after 48 h incubation with cytokines. Data is presented as mean±SE (n=3); P<0.05, *P<0.001.
Figure 5:
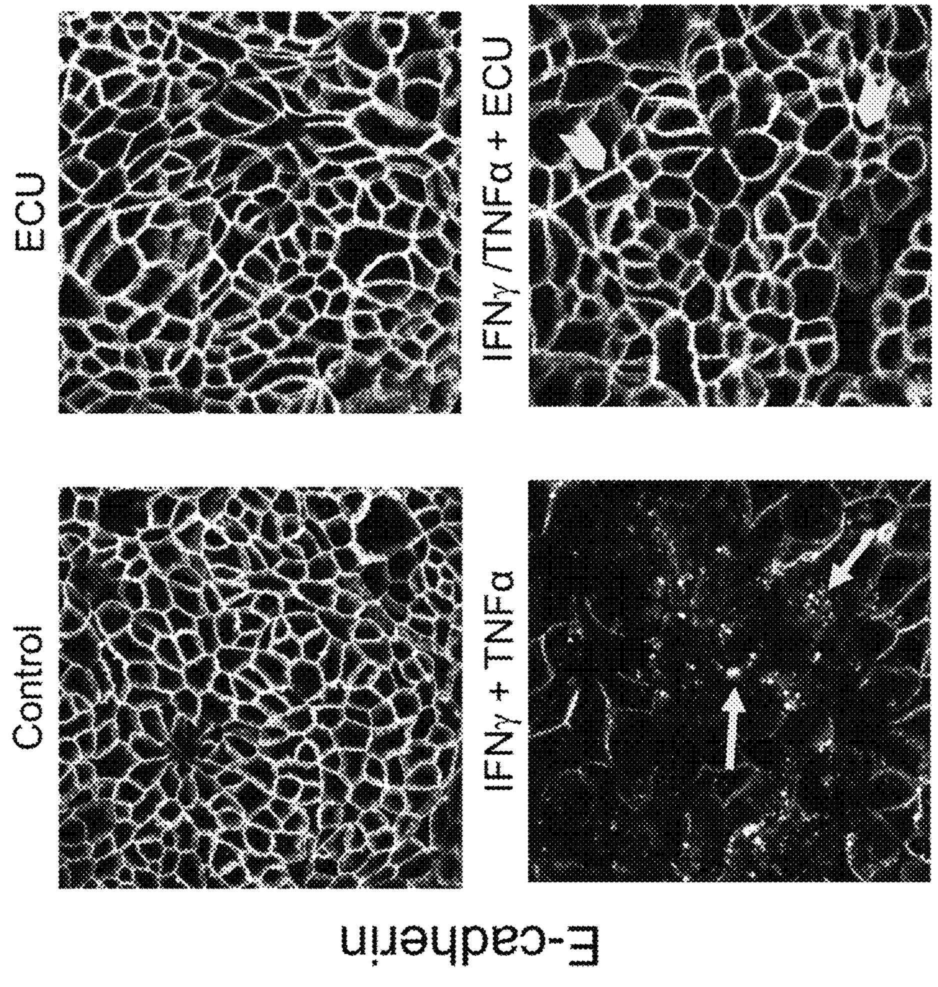
FIG. 5: E-cadherin-enhancing drugs prevent cytokine-induced disruption of epithelial adherens junctions. Confluent T84 cell monolayers were pretreated with either vehicle, or ECU (10 μM) for 24 hours. Afterwards, cells were exposed to a combination of TNFα (10 ng/ml) and IFNγ (50 ng/ml) with and without ECU for 48 h. Cells were fixed and structure of adherens was determined by immunolabeling of E-cadherin. Arrows point on disruption of normal E-cadherin labeling in cytokine-exposed, vehicle-treated cells. Arrowheads indicate a dramatic suppression of cytokine-induced disruption of adherens junctions after ECU treatment.
Figure 6:
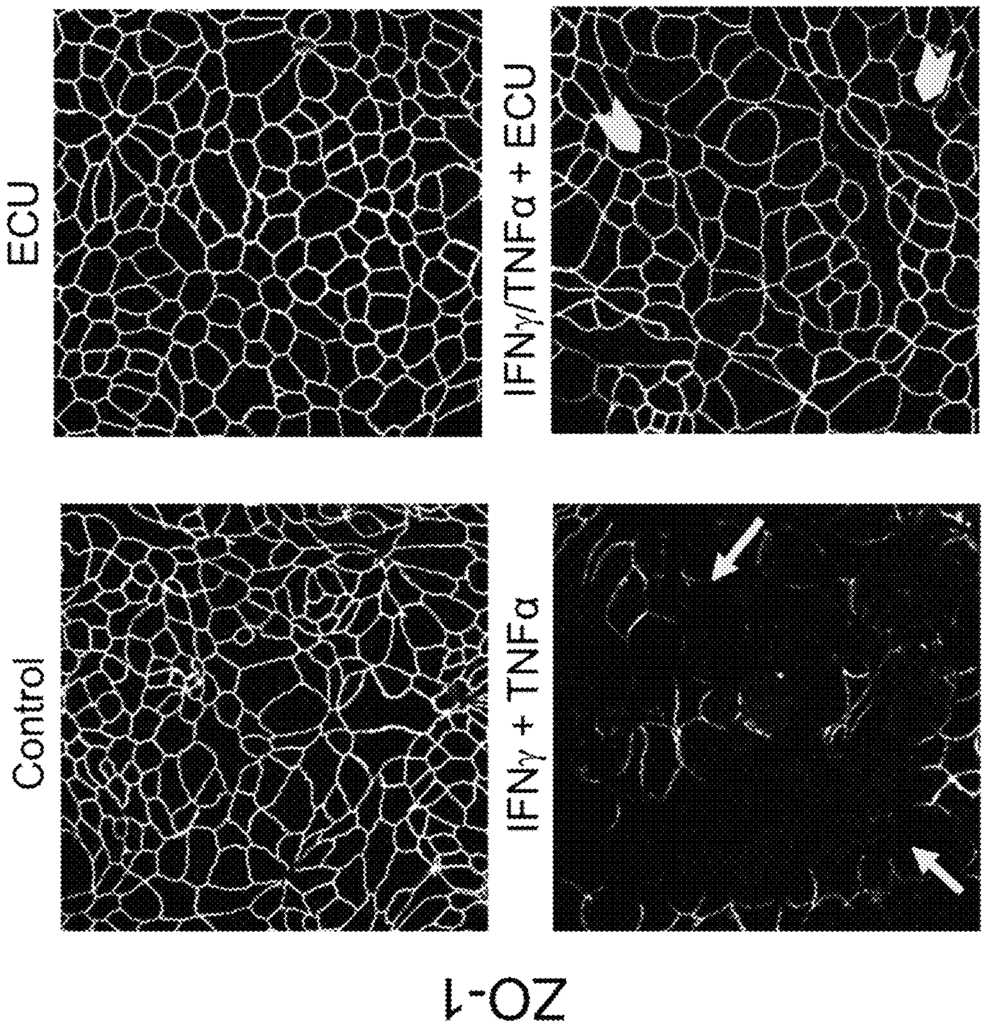
FIG. 6: E-cadherin-enhancing drugs prevent cytokine-induced disruption of epithelial tight junctions. Confluent T84 cell monolayers were pretreated with either vehicle, or ECU (10 μM) for 24 hours. Afterwards, cells were exposed to a combination of TNFα (10 ng/ml) and IFNγ (50 ng/ml) with or without ECU for 48 h. Cells were fixed and structure of tight junctions was determined by ZO-1 immunolabeling. Arrows point on disruption of normal ZO-1 labeling in cytokine-exposed, vehicle-treated cells. Arrowheads indicate inhibition of cytokine-induced tight junction disruption after ECU treatment.
Figure 7:
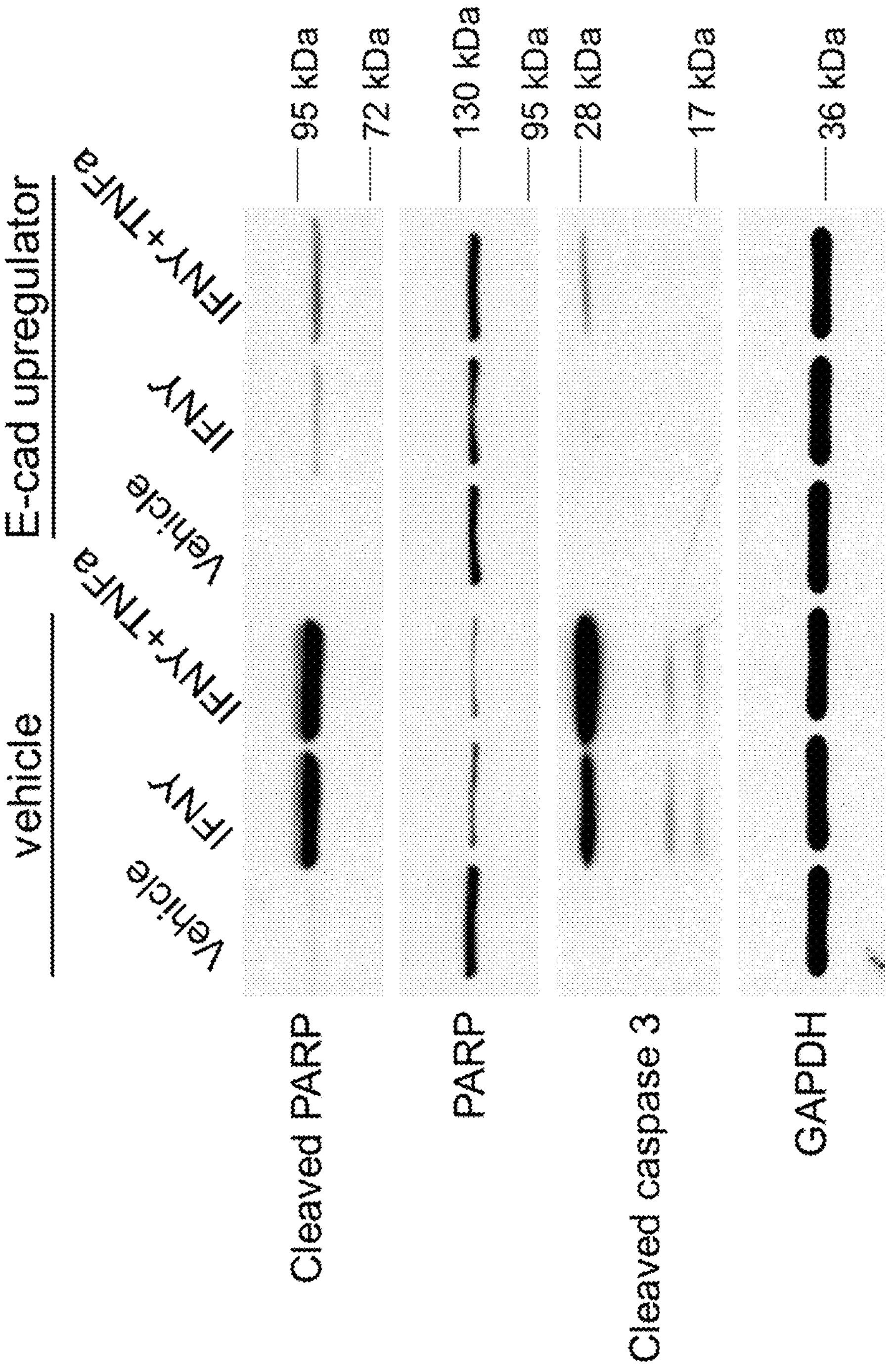
FIG. 7: E-cadherin-enhancing drugs attenuate cytokine-induced cell death. Confluent T84 cell monolayers were pretreated with either vehicle, or ECU (10 μM) for 24 h. Afterwards, cells were exposed to either IFNγ (50 ng/ml) alone, or its combination with TNFα (10 ng/ml) with and without addition of ECU for additional 48 h. Cell were lysed and levels of different apoptotic markers were determined by immunoblotting analysis.

Next, it was investigated if E-cadherin-enhancing drugs can block disruption of the intestinal epithelial barrier caused by proinflammatory cytokines commonly upregulated in the intestinal mucosa during Inflammatory Bowel Diseases and other gastrointestinal disorders. A combination of two cytokines were selected: tumor necrosis factor alpha (TNFα, 10 ng/ml) and interferon-gamma (IFNγ, 50 ng/ml), which are known to compromise barrier integrity and trigger apical junction disassembly in cultured epithelial cell monolayers and intestinal mucosa in mice. Indeed, 48 hour incubation of well-differentiated T84 cell monolayers with TNFα and IFNγ caused a dramatic decrease in TEER (FIGS. 3A, 4A) and increase in transepithelial dextran flux (FIGS. 3B, 4B), which indicates the increase in barrier permeability. Pre-treatment of cell monolayers with either ECU (FIG. 3), or ML327 (FIG. 4) markedly attenuated such cytokine-induced disruption of the epithelial barrier. Next, it was examined if ECU protects epithelial adherens junctions (AJ) and tight junctions (TJ) from cytokine-induced disassembly. Immunofluorescence labeling of a specific AJ marker, E-cadherin, and a TJ marker, ZO-1, was used to visualize structure of different junctional complexes. Control epithelial monolayers displayed a prominent 'chicken wire' labeling pattern for all tested AJ/TJ proteins, which is characteristics of intact epithelial junctions (FIGS. 5, 6). This labeling pattern was markedly disrupted by TNFα/IFNγ exposure, revealing cytokine-induced AJ and TJ disassembly (arrows). Interestingly, ECU treatment while having little effect on the normal AJ and TJ structure, completely prevented cytokine-induced junctional disassembly (FIGS. 5, 6, arrowheads). Since epithelial barrier-disruptive effects of IFNγ could be partially explained by excessive epithelial apoptosis (cell death) triggered by this cytokine, the effects of ECU on IFNγ-induced apoptosis were investigated. Immunoblotting analysis demonstrates that 48 hour exposure of T84 cell monolayers to either IFNγ alone, or TNFα/IFNγ pair caused significant cell apoptosis manifested by disappearance of intact full-length PARP protein and appearance of a cleaved PARP fragment along with cleaved (active) caspase-3 (FIG. 7). Interestingly, ECU prevented cytokine-induced PARP cleavage and caspase-3 activation, thereby indicating inhibition of apoptosis (FIG. 7). Overall, this series of the experiments demonstrates that E-cadherin-enhancing drugs strengthen a steady-state barrier in normal human intestinal epithelial cell monolayers and prevent barrier disruption and epithelial junction disassembly caused by proinflammatory cytokines. The barrier-protective effects of E-cadherin-enhancing drugs in inflamed intestinal epithelium could be at least partially mediated by inhibition of cytokine-induced epithelial cell apoptosis.

Figure 8:
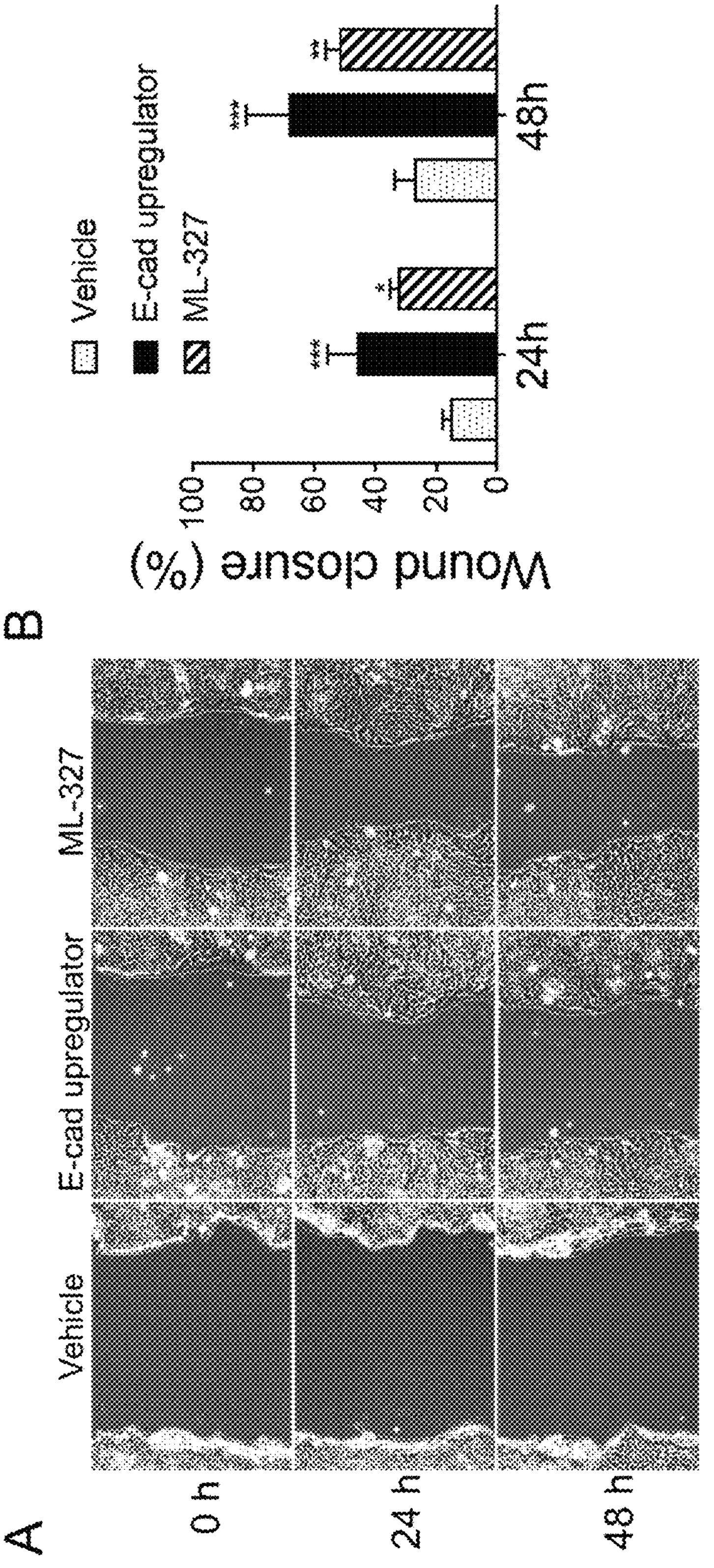
FIG. 8: E-cadherin-enhancing drug promote collective migration of intestinal epithelial cells. Confluent T84 cell monolayers were pretreated with either vehicle, ECU (10 μM) or ML327 (10 μM) for 24 hours. Afterwards, cell monolayers were wounded and allowed to migrate into wound area in the presence of the drugs. Cell monolayers were photographed and wound closure was calculated at the indicated times. Data is presented as mean±SE (n=3); P<0.05, *P<0.01.
Figure 9:
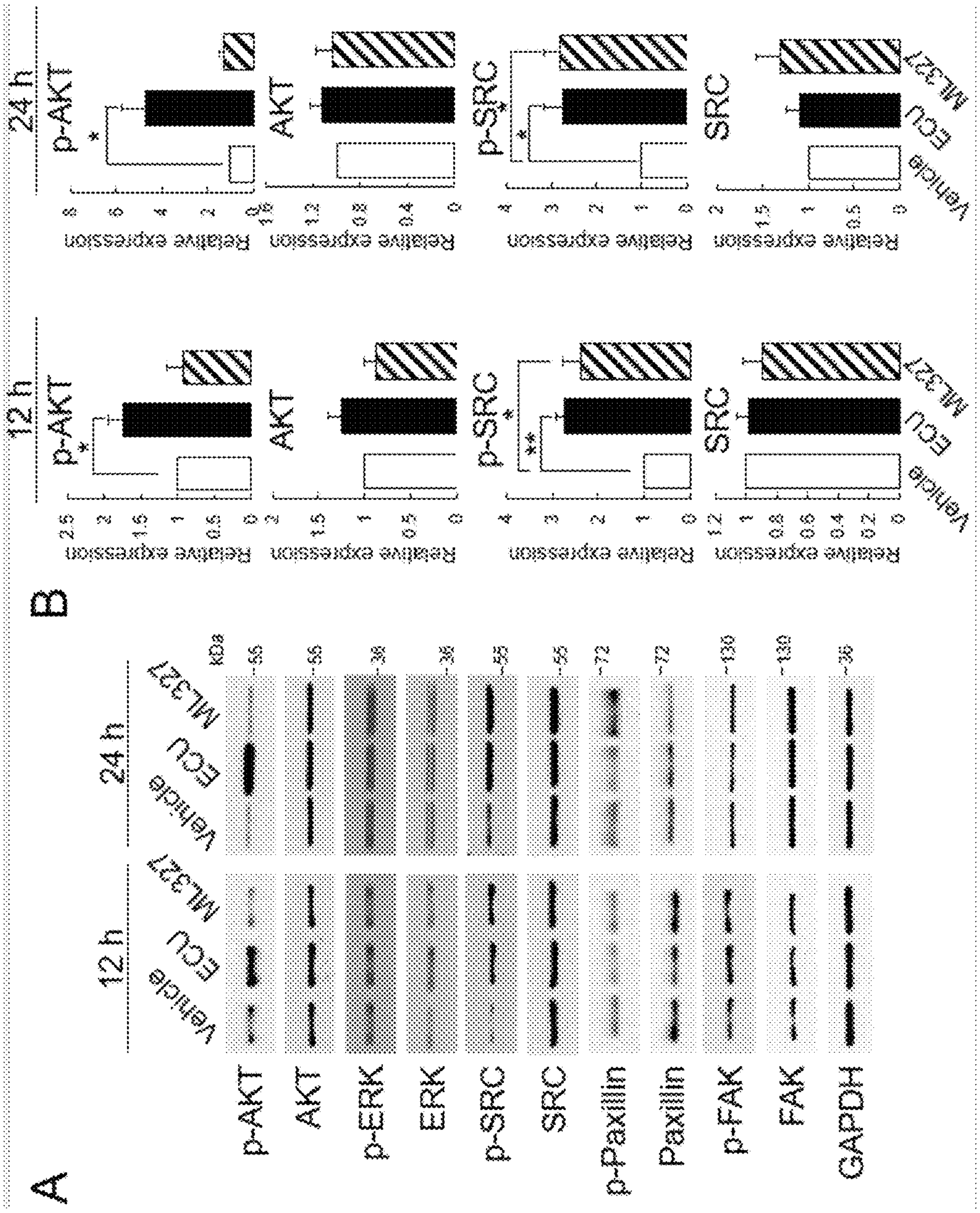
FIG. 9: Accelerated wound healing in ECU and ML327-treated epithelial cells is accompanied by the activation of pro-migratory signaling events. Confluent T84 cell monolayers were pretreated with either vehicle, ECU (10 μM), or ML327 (10 μM), for 24 h, and were subjected to multiple wounding. Total cell lysates were collected at 12 and 24 h post-wounding, and the expression of different signaling molecules was determined by immunoblotting. Representative immunoblots (A) and densitometric quantification of protein band intensities from three independent experiments (B) are shown. Data are presented as a mean±SE (n=3); *p<0.05; **p<0.01.

Finally, the effects of E-cadherin-enhancing drugs on epithelial restitution (wound healing) were examined. This is an important question given the fact that epithelial wounds are frequently formed in inflamed intestinal mucosa of IBD patients and wound healing is necessary to restore the integrity of the gut barrier and to achieve remission of chronic inflammatory diseases. Confluent T84 cell monolayers were pre-incubated with either ECU, ML327 or vehicle. Afterwards, the monolayers were wounded and allowed to migrate for 24-48 hours. FIG. 8 shows that both E-cadherin-enhancing drugs significantly increased migration of T84 cells during wound healing. Similar increase in cell migration was observed in HT-29 human colonic epithelial cells and IEC6 rat small intestinal epithelial cell monolayers exposed to either ECU, or ML327 (data not shown), thereby indicating that this phenomenon is not a selective feature of T84 cells. Together, these data suggest that the isoxazole-based compounds (ECU, ML327 and their derivatives) act as potent barrier-protective agents in the inflamed and injured intestinal epithelium by stabilizing epithelial junctions and promoting epithelial restitution.

All publications and patents mentioned in the specification and/or listed below are herein incorporated by reference. Various modifications and variations of the described methods, compositions, and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope described herein.

I claim:

1. A method of treating an inflammatory bowel disease having intestinal mucosal injury comprising:

administering to a subject a composition comprising an agent that up-regulates the expression of E-cadherin, wherein said agent is small molecule selected from the group consisting of ML327 (N-(3-(2-hydroxynicotinamido) propyl)-5-phenylisoxazole-3-carboxamide), which has the following structure:

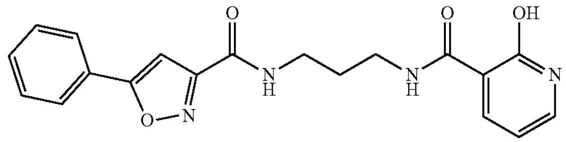

ML327 and E-cadherin Up-Regulator (ECU; 5-(Furan-2-yl)-N-(pyridine-4-yl)butyl)isoxazole-3-carboxamide), which has the following structure:

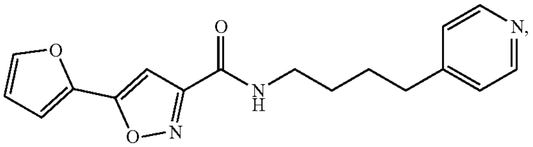 [SMILES: O=C(NCCCCc1ccncc1)c1cc(-c2ccco2)on1]

wherein said subject has an inflammatory bowel disease that comprises intestinal mucosal injury, and wherein said administering of said composition: i) prevents cytokine induced disruption of epithelial adheren junctions, and ii) stimulates increased wound healing of said intestinal mucosal injury by increasing migration of intestinal epithelial cells.

2. The method of claim 1, wherein said inflammatory bowel disease condition is ulcerative colitis.

3. The method of claim 1, wherein said subject is a human.

4. The method of claim 1, wherein said composition is administered to the bowel of said subject.

5. The method of claim 1, wherein the composition is administered systemically to the subject.

6. The method of claim 1, wherein the composition is administered locally to a site of inflammation in said subject.

7. The method of claim 1, wherein the composition is formulated as a suppository and is administered rectally.

* * * * *